United States Patent
Sailer et al.

(10) Patent No.: US 12,426,601 B2
(45) Date of Patent: Sep. 30, 2025

(54) FUNCTIONAL MICROBIOLOGICAL COATING

(71) Applicant: Biofinish International B.V., Deventer (NL)

(72) Inventors: Michael Fritz Sailer, Pijnacker (NL); Franciscus Antonius Van Rooijen, Deventer (NL); Stephanie Rensink, Winterswijk (NL)

(73) Assignee: Biofinish International B.V., Deventer (NL)

( * ) Notice: Subject to any disclaimer, the term of this patent is extended or adjusted under 35 U.S.C. 154(b) by 345 days.

(21) Appl. No.: 17/762,572

(22) PCT Filed: Sep. 23, 2020

(86) PCT No.: PCT/NL2020/050585
§ 371 (c)(1),
(2) Date: Mar. 22, 2022

(87) PCT Pub. No.: WO2021/060978
PCT Pub. Date: Apr. 1, 2021

(65) Prior Publication Data
US 2022/0330553 A1    Oct. 20, 2022

(30) Foreign Application Priority Data
Sep. 23, 2019  (EP) .................... 19199009

(51) Int. Cl.
| *A61K 36/06* | (2006.01) |
| *A01N 25/04* | (2006.01) |
| *A01N 63/30* | (2020.01) |
| *C09D 5/14*  | (2006.01) |
| *C12N 1/14*  | (2006.01) |

(52) U.S. Cl.
CPC ............ *A01N 63/30* (2020.01); *A01N 25/04* (2013.01); *A61K 36/06* (2013.01); *C09D 5/14* (2013.01); *C12N 1/14* (2013.01); *C12N 2500/76* (2013.01); *C12N 2533/50* (2013.01); *C12N 2533/72* (2013.01)

(58) Field of Classification Search
None
See application file for complete search history.

(56) References Cited

U.S. PATENT DOCUMENTS
| 5,534,252 A     | 7/1996 | McAfee et al. |
| 2008/0226847 A1 | 9/2008 | Beakler       |

FOREIGN PATENT DOCUMENTS
| EP | 1704028 B1    | 2/2011  |
| GB | 24595 A       | 10/1914 |
| WO | 2012119228 A1 | 9/2012  |

OTHER PUBLICATIONS

Pouliot et al. Biomacromolecules 6: 1122-1131, 2005.*
Rensink et al., "Quality determination of Aureobasidium cells in the fermentation liquid of a wood protective biofinish" Fungal Biology, vol. 115, Oct. 1, 2011 (Oct. 1, 2011), 1008-1018, Amsterdam, NL, XP055651929.
Van Nieuwenhuijzen et al., "The fungal composition of natural biofinishes on oil-treated wood", Fungal Biol. Biotechnol. (2017) 4:2, 13 pages.
Bozoudi et al., "The Multiple and Versatile Roles of Aureobasidium pullulans in the Vitivincultoral Sector", Fermentation, vol. 4, No. 4 (2018), 85, 15 pages.

* cited by examiner

*Primary Examiner* — S. Devi
(74) *Attorney, Agent, or Firm* — Verrill Dana, LLP

(57) ABSTRACT

The present invention refers to a coating composition comprising a suspension of a microorganism, wherein the suspension comprises a pigmented vegetative cell, an unpigmented vegetative cell and a pigmented chlamydospore of the microorganism, and a surfactant ranging from 130 g/mol and 1500 g/mol. The invention further relates to a method for the preparation of the coating composition, a method for application coating one or more coating pre-layers and curing a material, a coated material obtainable by this method and a method for refreshing the coating of the coated material.

14 Claims, 7 Drawing Sheets

Melanin producing cells in a petri dish

Wavelengths of natural radiation

Substitute sheet(s) drawings (Rule 26)

Dark pigmented chlamydospores (arrows) and vegetative cells (light, small) in a fungal suspension (400x)

Water-based fungal suspension including a high content of chlamydospores

Wood surface comprising dried water based fungal suspension

Fig. 5

Pine wood surface comprising one (left) and two (right) microbial coating layers Pine wood coated with three layers of microbial coating,
2 years outdoor exposure Stability of the microbial coating on a wooden surface in the absence of a surfactant Samples after artificial ageing without presence of sufficient surfactants. The coating is washed off

Fig. 9A

Biological coating with lack of surfactants is easily removable in the filter test

Fig. 9B

Stability of the microbial coating on a wooden surface in the presence of a surfactant Samples after artificial ageing with sufficient surfactants. The coating remains stable.

Fig. 9C

Biological coating with sufficient surfactants is hardly removed in the filter test

Fig. 9D

FUNCTIONAL MICROBIOLOGICAL COATING

The present invention refers to a coating composition comprising a suspension of a pigmented microorganism, in particular pigmented and unpigmented vegetative cells and spores, and a surfactant, to a method for is production, to a method of coating a material and to a coated material.

TECHNICAL BACKGROUND

The durability and aesthetics of materials, in particular biodegradable materials such as wood, is in practice usually accomplished by applying surface treatments (coatings) which contain a number of different substances like e.g. binders, pigments and organic biocidal compounds. From an environmental and health viewpoint, the use of such biocidal compounds is undesired and more and more limited. Accordingly, environmental and health regulations put more and more strict limitations on the use of such compounds.

Thus, there is a continuous need for environmentally friendly materials with a satisfactory resistance against deterioration due to the destructive influence of microorganisms and/or weather-effects, such as UV-radiation and moisture.

The interaction of microorganisms with surfaces has important implications in a range of areas, including bioenergy, biofouling, biofilm formation, or the infection of plants and animals. Many of the interactions of microorganisms with surfaces produce changes in the expression of genes that influence cell morphology and behavior, including genes essential for motility and surface attachment. Adhering to surfaces provides microorganisms with many advantages. Attachment to horizontal surfaces stimulates for example growth (particularly in nutrient-poor environments) as organic material suspended in liquid settles, is deposited on surfaces, and increases the local concentration of nutrients.

Microorganisms attached to surfaces often exist as a type of biofilm even if not all characteristics of a biofilm are fulfilled. For example surfaces of painted or unpainted wood or metal covered with one or more (artificially) applied layers of a microbiological coating at least partly consisting of a living fungus such as *Aureobasidium* cells are called a biofinish which is considered to be a functional coloration (i.e., pigmentation) and protecting cover, respectively. The pigmentation of a biofinish is together with its presumed protection and self-healing properties, an important ingredient of a sustainable solution for a biocide free wood finish system.

The challenge of most fungal cells however is to survive on the long term on exposed surfaces (regardless of the material). Temperatures between -20° C. and 80° C., low water availability over longer periods, mechanical stress caused by wind and sand/salt, changing pH-values and a strong UV-radiation demand an extraordinary performance of the biofinish, especially of the fungal cells. In order to survive under these conditions thick walled pigmented fungal cells with a very low biological activity and the potential to produce extracellular polymeric substance (EPS) possess the potential to interact are needed. Chlamydospores also called "resting spores" fulfil these requirements. Therefore at least a minimum share of chlamydospores is necessary in a microbiological coating. From a technical and economical point of view a fast drying coating (e.g., drying within minutes) with a stable water-resistant attachment to the surface of the materials is required. The main problem to be solved using a coating consisting of live cells is a fast and reliable adhesion on the carrier material and the different microbial coating layers. If this process is not properly carried out the microbiological coating will not dry and adhere on the surface. In case of rain the microbial coating would completely be washed away and removed as long as it is not waterproof.

There is a wide variety of methods for the protection of surfaces. U.S. Pat. No. 5,534,252 for example relates to a method for controlling sapstain in wood, wherein otherwise untreated wood is steam pasteurised and then dipped in a spore solution containing spores of a fungus from the class Hyphomycetes.

WO 2012/119228 A1 describes the use of different pigmented fungi to apply colours on wood surfaces. The different fungi consist of pigmented basidiomycetes and ascomycetes. Many of these fungi use wood as a carbon source and are known as wood degrading fungi. However after the fungi invaded the wood the pieces have to be sterilized to avoid wood degradation, which is suggesting that there are no fungal cells alive. This is further an indication that the treated products are not protected and cannot be used in outdoor conditions without further treatment since no protecting coating is on the surface.

GB24595 A A.D. 1913 describes the colouration and protection of wood using mainly *Chlorosplenium aeruginosum* a fungus also using wood as a carbon source. In order to treat the wood the fungus has to grow into the substrate which has to be sterilized in advance. Furthermore, the surrounding has to be sterile, which makes it practically very difficult to treat larger amounts of timber and use this method in an industrial process. In order to prevent wood degradation the growth of the fungus has to be stopped by sterilisation after a certain time.

US2008/226847 A1 describes a wood colouration principle which is derived from the pigmentation caused by at least 2 different fungi invading thin wood veneers. This method is similar to the method of WO 2012/119228. Since in this case also wood degrading fungi are used a sterilizing step has to be applied after wood invasion by the fungi to avoid wood degradation.

EP 1 704 028 131 describes a method of treating wood with a water insoluble substance which is for example *Aureobasidium* and optionally a growth substrate. The fungal cells have to develop and grow on the surface treated with nutrients and it may take several months to achieve a homogeneous surface depending on the environmental conditions. If a surface is positioned at a place without any moisture availability for example an esthetical acceptable functional microbial coating is hardly formed and additional effort is necessary to create an appropriate environment for the microorganism. Nieuwenhuijzen at al. (2017) are describing the occurrence of fungi on oil treated wood during outdoor exposure. Since the growth of the fungi took place in a natural way a long time of growth is required to achieve a homogeneous colour. Nieuwenhuijzen at al. mainly describe the same effects as mentioned in EP 1 704 028 B1.

Rensink et al. 2017 describe a method to assess the occurrence of living cells after thermal treatment. At least some cells of the fungus *Aureobasidium* can survive higher temperatures. No further indication is given about the role of chlamydospores and the functionality of the viable cells.

Bozoudi et al. 2018 describe the potential of *Aureobasidium* to produce a large range of chemical substances in fermentation processes. Some of these substances are useful in different areas. No outdoor applications on solid materials and different climate conditions are mentioned.

In addition, none of the fungal coatings or methods for the preparation of fungal coatings of the prior art describe the occurrence of binders and surfactants (neither artificially added nor produced by the fungus itself) required to form functional coating layers with sufficient chemical adhesion of the fungal cells according to the present invention. Since the wood is sterilized according to prior art no living fungal cells of the original fungus remain to maintain long term protecting properties.

All these coatings and methods for coating are significantly different from the present invention of coating a surface with layers consisting of living fungal cells forming coating layers which remain alive over the whole period of use. The fungal cells metabolize added carbon hydrates and optionally produce surfactants. Therefore, the fungal coating layers protect the carrier material.

The present invention further provides long- and short-term resistance against deterioration due to degrading microorganisms and/or weather effects such as UV-radiation and moisture. In addition, the coating of the present invention provides mechanical stability based on one or more coating layers which are technically applied on a surface such as wood, metal, glass or plastic.

To be able to technically apply a useful microbial coating some requirements however have to be met:
  drying of the coating within a reasonable time (preferably) few minutes
  fast and stable adhesion on the surface (substrate)
  living fungal cells being able to survive outdoor conditions (high temperatures, low water availability) over a long period of time.

The advantage of the technically application of one or more coating layers consisting of the present invention is that the material and/or the surface (substrate) does not have to be sterilized. Thus, the application process is substantially quicker and easier to be controlled than a process based on the fungal growth into the wood substrate according to prior art.

To control the performance of e.g. water resistant adhesion, the biochemical interaction between the fungal cells, additives and solid substrate has to be well balanced. The coating formulation has to be designed in such a way that the adhesion on the carrier material and/or surface (substrate) is created during the curing process. A curing process, which only consists of supply of energy in the form of heat to cause the evaporation of water, does not provide sufficient curing and adhesion forces to adhere one or more microbiological coating layers consisting of fungal cells.

To overcome this disadvantage and to improve the protection of a material and/or surface, the present invention can make use of a microorganism in its growth medium forming for example a microorganism suspension comprising or consisting of pre-activated dormant fungal cells such as chlamydospores. Optionally or in addition, molecular compounds such as surfactants with a molecular weight between 130 g/mol and 1500 g/mol (e.g., per repetitive unit) are added to the microorganism suspension forming the coating composition or part thereof to improve growth and biochemical interaction of the fungal cells on the surface.

Furthermore, the quality of the coating composition is for example influenced by the cell types of the microorganism such as a combination of pigmented and/or unpigmented vegetative cells and pigmented and/or unpigmented pre-activated dormant chlamydospores.

SUMMARY

The present invention relates to a coating composition comprising a suspension of a microorganism, wherein the suspension comprises at least pigmented and unpigmented vegetative cells, and a pre-activated chlamydospore of the microorganism, and a surfactant of high and/or low molecular weight. The term surfactant refers to ionic and/or non-ionic surfactants with a molecular weight between 130 g/mol and 1500 g/mol per repetitive unit. The surfactant is for example selected from the group consisting of a lipopeptide, a lipid, a glycolipid, a uronic acid based polymer, heavy oil, e.g., mannitol oil (e.g., liamocin), siderophore, malic acids and/or a derivate thereof, polysorbates and/or a derivate thereof, sorbitane, a pectine, a glucomannan or a derivative thereof, or a combination thereof. For example the surfactant is at least partly produced by the microorganism. The surfactant is for example present in the composition in an amount of 2 g/l to 10 g/l, 3 g/l to 9 g/l or 5 g/l to 8 g/l.

The microorganism is for example a fungus, a bacterium or a combination thereof. The fungus is for example selected from the group consisting of Aureobasidium, Rhodotorula, Lapidomyces, Superstratomyces, Sarcinomyces, Rhizospaera, Chrysosporium Penicillium, Alternaria, Fusarium, Stachybotrys, Taphrina, Sydowia, Phacidiella, Pyrenochaeta, Phaeococcomyces, Knufia, Capronia, Cladosporium, Cryptococcus, Pleurophoma, Cynanodermella, Exophiala, Epicoccum, Didymellaceae or a combination thereof. In one embodiment the fungus is Aureobasidium, Rhodotorula or a combination thereof.

The spore of the coating composition is for example at least a pigmented and/or an unpigmented chlamydospore. The unpigmented chlamydospore optionally becomes pigmented at a later stage The coating composition further comprises for example a water-soluble binder, a water-insoluble binder, a thickener or a combination thereof. The binder is for example an extracellular polymeric substance (EPS) such as a hetero polysaccharide, pullulan, chitin, proteoglycan, β-glucan, polymalic acid, uronic acid based polymer, glycoprotein or a combination thereof. The thickener is for example selected from the group consisting of alginic acid and/or a derivate thereof, agar-agar, carrageenan and/or a derivate thereof, locust bean gum (LBG), tara gum, tragacanthin, gum arabic, gum karaya, xanthan, tannins from e.g. T. spinose, gellan gum or a combination thereof.

The term thickener refers to a substance from the above mentioned group able to interact with microbial cells such as bacterial or fungal cells and/or EPS in order to create with or without microbial such as fungal or bacterial interaction a water-resistant biochemical bonding to the carrier material surface.

The viscosity of the coating composition is for example in the range of 100 to 3.000 mPa at 20° C.

The present invention further refers to a method for the preparation of the coating composition. This method comprises for example the steps:
  growing a microorganism in a growth medium comprising a carbohydrate source to stimulate the production of the surfactant ranging from 130 g/mol and 1500 g/mol, the binder or a combination thereof by the microorganism, harvesting the microorganism with the growth medium to form the coating composition, and optionally adding the surfactant ranging from 130 g/mol and 1500 g/mol, the binder, the thickener or a combination thereof to the coating composition;

or growing a microorganism in a growth medium comprising a carbohydrate source, e.g., a potato medium, to stimulate the production of the surfactant ranging from 130 g/mol and 1500 g/mol, the binder or a combination thereof by the microorganism, optionally isolating the microorganism from the growth medium, dissolving the microorganism in a composition comprising a carbon source for example an oil, the low and/or high molecular weight surfactant ranging from 130 g/mol and 1500 g/mol, the binder or a combination thereof to form the coating composition, and optionally adding the carbon source such as the low and/or high molecular weight, surfactant ranging from 130 g/mol and 1500 g/mol, the binder, the thickener or a combination thereof to the coating composition.

The microorganism is for example grown under an adequate standard fermentation condition. The term adequate standard fermentation condition refers to a fermentation which is carried out at e.g. a temperature between 25° C.-35° C., stirring speed between 50 and 700 rpm, air debit>1 l/min, $DO_2$ between 0% and 90%, pH controlled fluctuating between 2 and 7.

The carbohydrate source is for example a biological waste material such as marc from straining fruit or vegetable such as remaining plant material from sugar production, wine production, juice production or a combination thereof.

The coating composition is further formulated by adapting the composition in a way that it is in a non-sterile surrounding (for example after opening) not easily infected by other micro-organisms and able to be stored for a long period allowing the pre-activated cells to survive.

In addition, the present invention is directed to a method for coating a material, for example comprising the steps:

applying the coating composition to the material at a temperature above 20° C., i.e., between 20 to 30° C. such as 20° C., 23° C., 25° C., 28° C. or 30° C., and drying the coating composition via natural or artificial radiation applying energy in the range of 50 to 5.000 mW/cm².

The radiation applied is for example UV radiation consisting of 50%-90% UV-A (380-315 nm) and 10%-50% UV-B (315-280 nm), or 60%-95% UV-A (380-315 nm) and 5%-40% UV-B (315-280 nm).

The material for coating is for example selected from the group consisting of wood, metal, steel, plastic, concrete, finery, ceramic, stone or a combination thereof.

The coating composition is applied to the material forming one or more coating layers, each achieving for example a total thickness in the range of 0.1 to 1000 μm.

Furthermore, the present invention refers to a coated material obtainable by a method for coating material according to the present invention.

Moreover, the present invention is directed to a method for refreshing the coating of the coated material, wherein a nutrition medium is applied to the coated material comprising mineral oil, wax, vegetable- and/or animal oil including a derivative thereof, a water-insoluble substance of C4 to C32 saturated or unsaturated fatty acid ester, an amino acid, a pentosane or a combination thereof, and optionally a pigmented vegetative cell, an unpigmented vegetative cell and a pigmented chlamydospore of a microorganism.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

More specifically, all referenced documents are incorporated by reference to the same extent as if each individual document was specifically and individually indicated to be incorporated by reference.

DESCRIPTION OF THE FIGURES

FIG. 5 depicts a wood surface after application and drying of the water based microbial suspension.

FIG. 9A to 9D shows stability of the microbial coating on a wooden surface in the absence of a surfactant (FIGS. 9A and 9B) and in the presence of a surfactant (FIGS. 9C and 9D)

DETAILED DESCRIPTION

Figure 1:
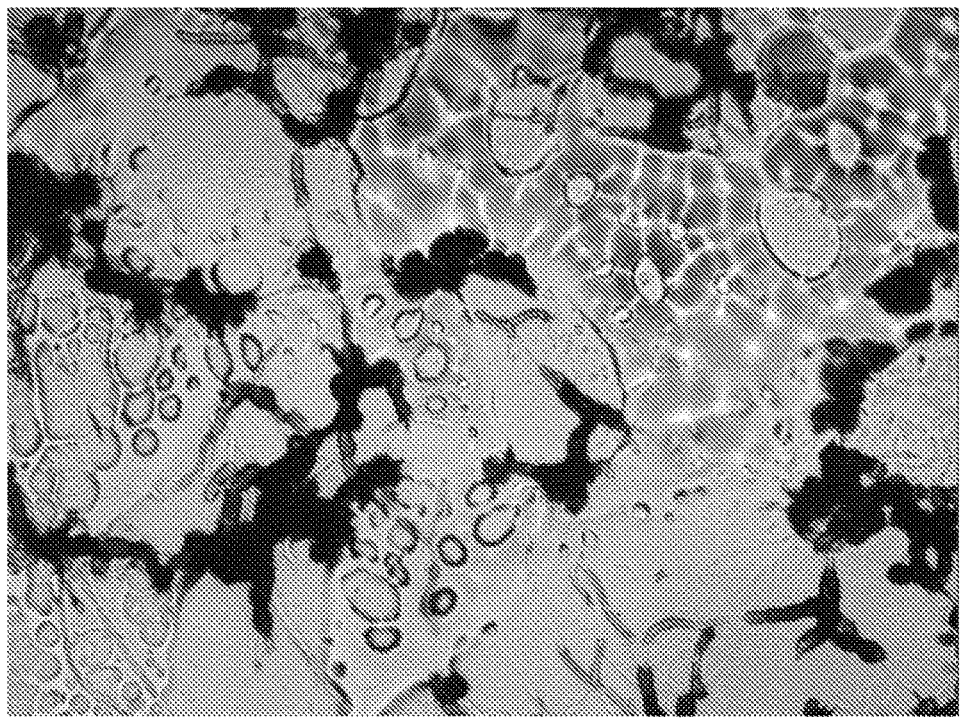
FIG. 1 depicts the pigment melanin as appearing in a vegetative cell, a spore or freely floating in a microorganism suspension such as a fungal or bacterial suspension.
Figure 2:
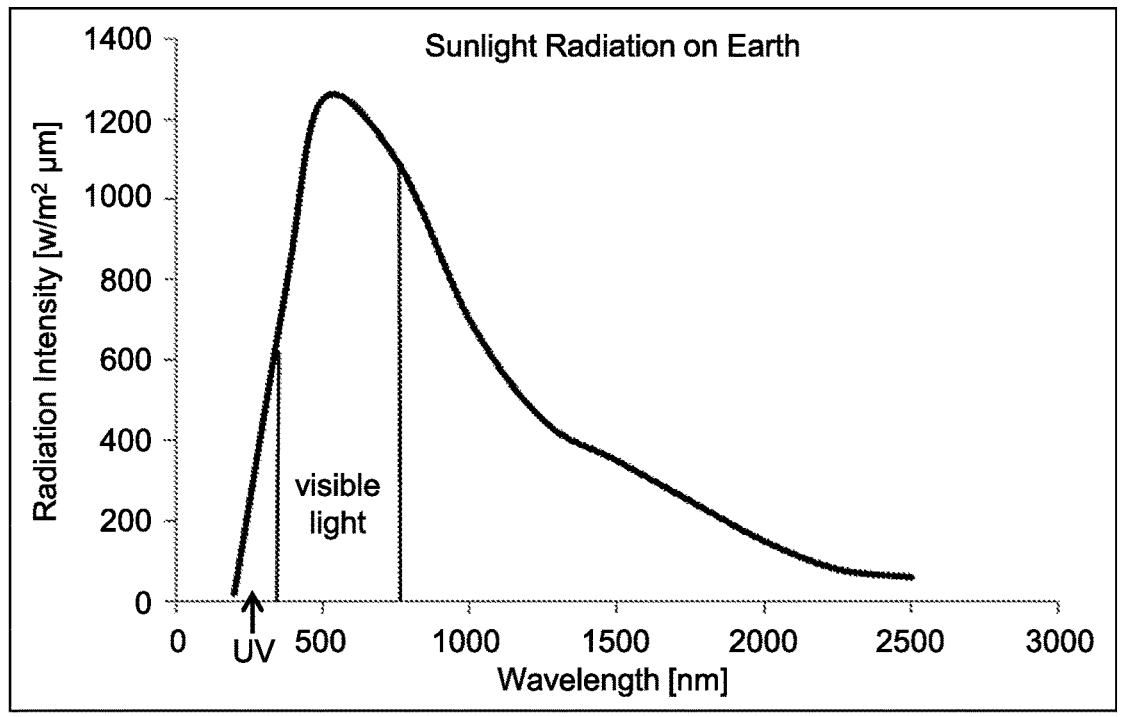
FIG. 2 shows wavelengths of natural radiation.
Figure 3:
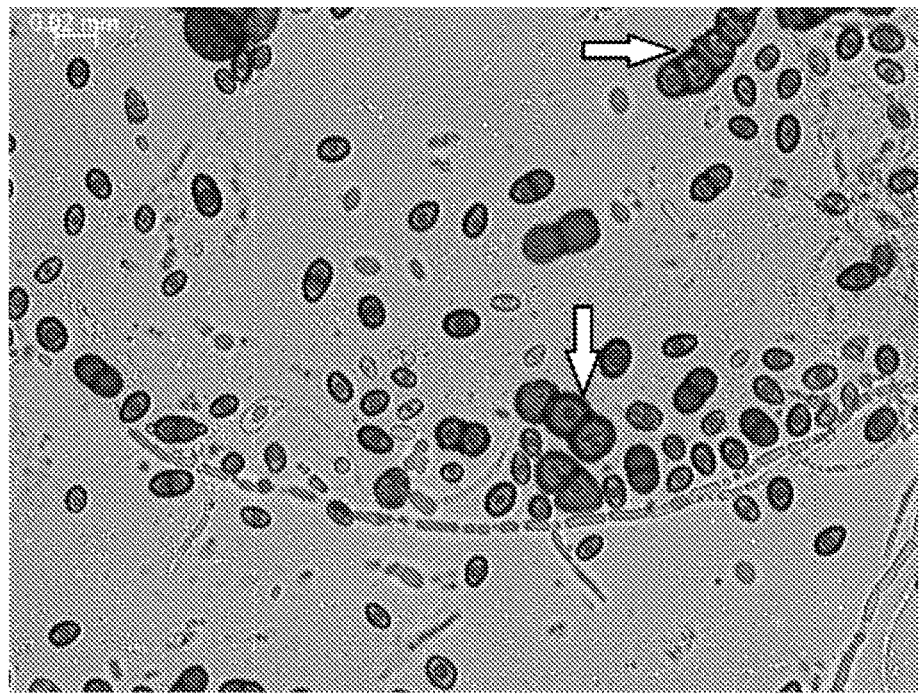
FIG. 3 shows round dark pigmented chlamydospores (indicated by arrows) and vegetative cells (light, small) in a fungal suspension (400×).
Figure 4:
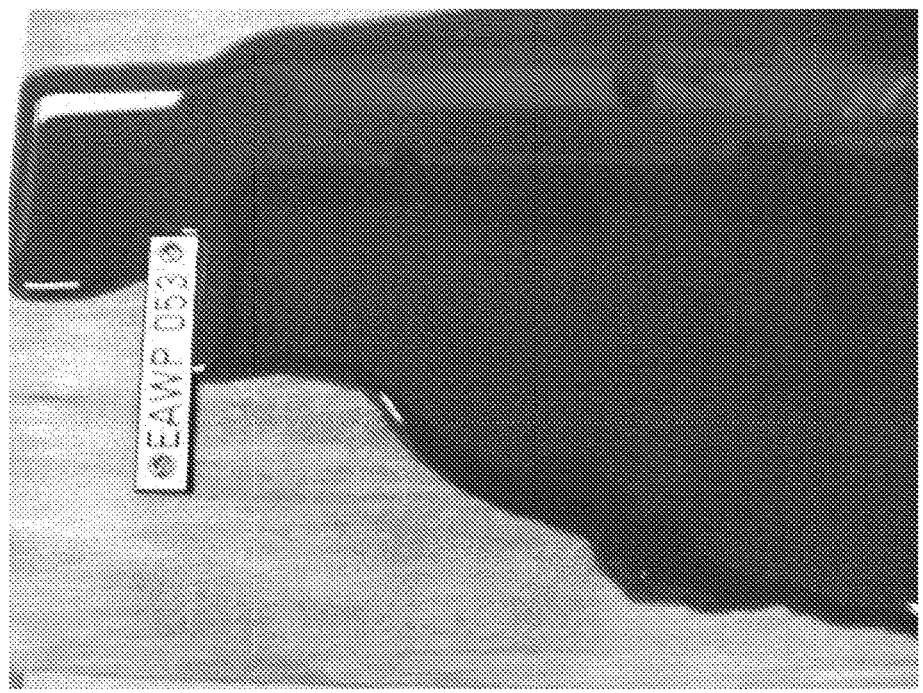
FIG. 4 shows the water-based fungal suspension with a high content of viable chlamydospores on a wood surface.
Figure 6:
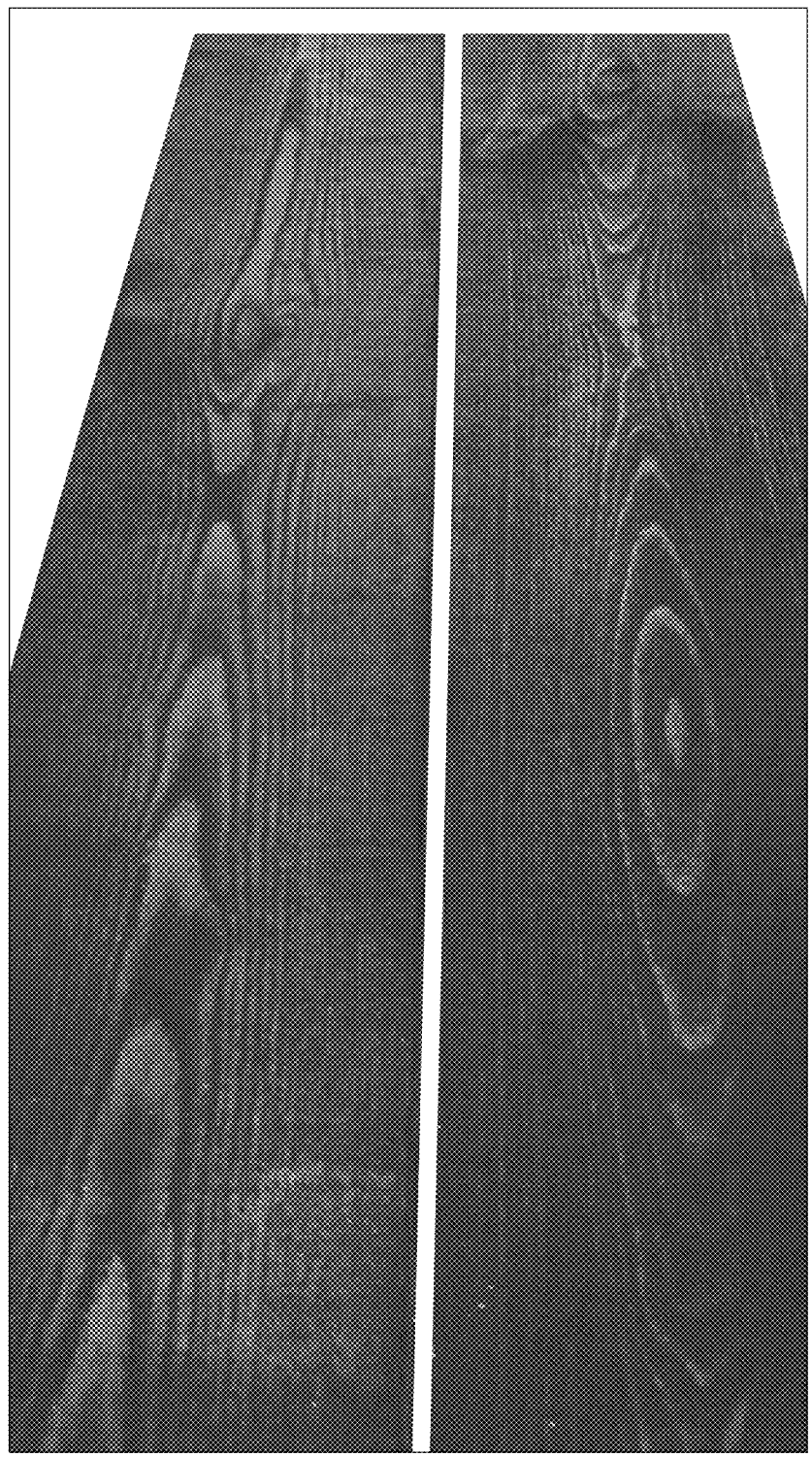
FIG. 6 shows a formulated microbial coating on a pine wood surface after curing. Left surface comprises one layer, right surface comprises two layers of the microbial coating.
Figure 7:
FIG. 7 shows a building element from pine wood coated with 3 layers of the microbial coating (dark elements) after 2 years outdoor exposure.
Figure 8:
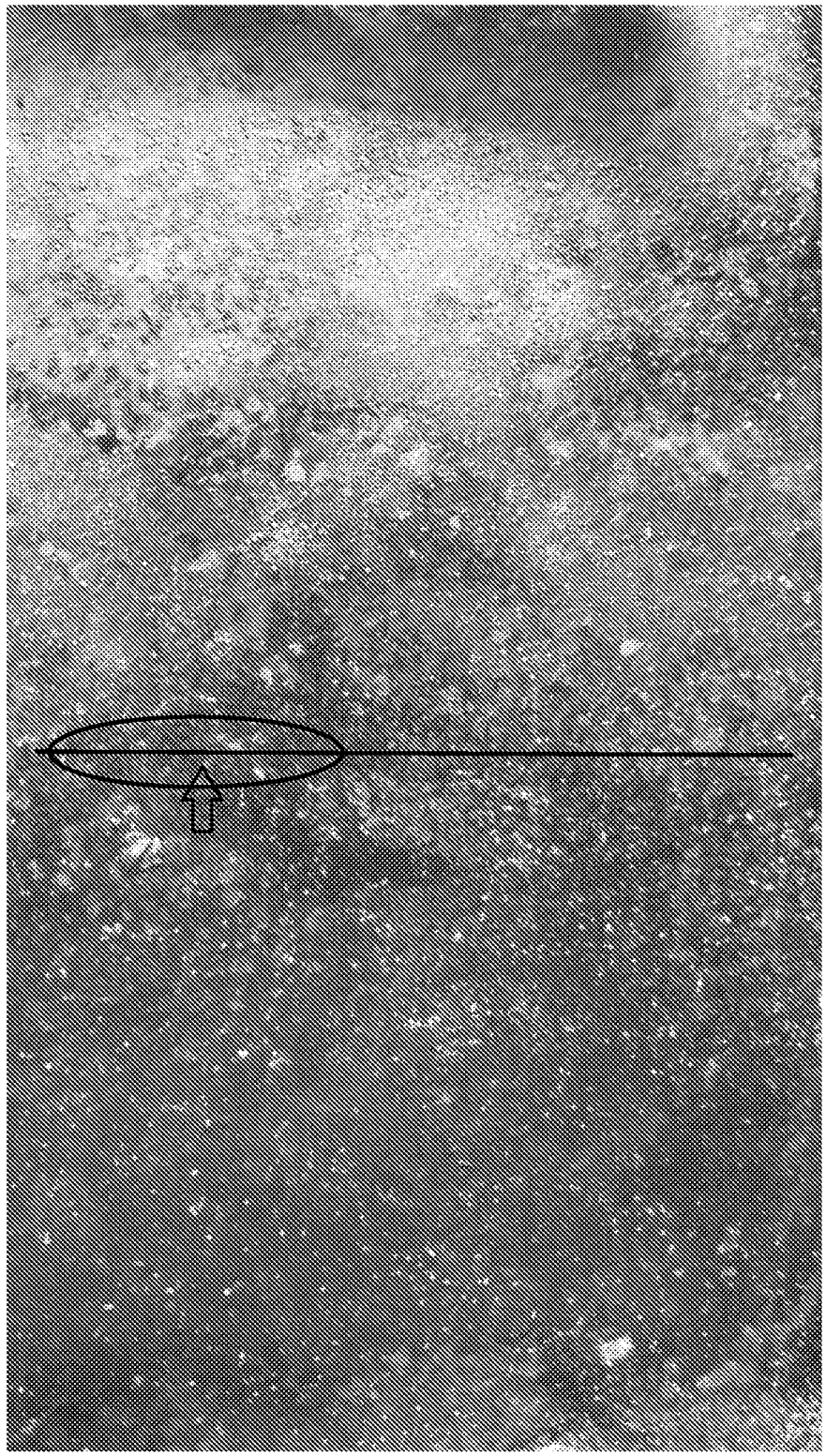
FIG. 8 depicts the microbial coating (right) and linseed oil on a metal surface (left) and untreated (centre ellipse) as a remedial treatment to reduce oxidation reactions. Compared to a linseed oil treatment (left) less rust is visible on the surface, indicating a corrosion inhibition effect.

The present invention is directed to a coating composition comprising a microorganism suspension, wherein the microorganism is, e.g., a fungus, a bacterium or a combination thereof. The suspension comprises pigmented and unpigmented vegetative cells and spores such as chlamydospores, which are pigmented and/or unpigmented. The coating composition is applied to a material in one or more layers, particularly to the surface of a material such as wood, metal, glass, steel, plastic, concrete, finery, ceramic, stone or any other material or combination of materials. It provides stable, long-term protection of the material against degradation. The material is cured using at least UV radiation consisting of 50%-90% UV-A (380-315 nm) and 10%-50% UV-B (315-280 nm), or 60%-95% UV-A (380-315 nm) and 5%-40% UV-B (315-280 nm).

The layers are applied by standard methods known to a person skilled in the art.

In the following, the elements of the present invention will be described in more detail. These elements are listed with specific embodiments, however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the present application unless the context indicates otherwise.

Throughout this specification and the claims, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

Under normal conditions even with higher temperatures the curing and water-resistant adhesion of the technically applied biological coating does not occur after several months even at elevated temperatures. The lack of suitable surfactants prevents obviously adequate adhesion on the material surface. Although the surface such as a wood surface is temporarily coloured the coating can easily mechanically be removed or washed away with water or other liquids which makes it unusable for application at outdoor conditions since it does not give the desired functionality like protection and colouration at outdoor conditions. Furthermore the coating becomes susceptible for microbial infections and degradation.

Surprisingly, the required water-resistant adhesion of the microbial coating layers on the material and/or surface and full functionality is achieved within several minutes, e.g., 5 to 45 min., 10 to 30 min. or 15 min., if the coating comprises a minimum amount of spores such as chlamydospores and surfactants produced for example by the fungus during the fermentation process. In contrast to most fermentation processes, the formation of a pigment such as the pigment melanin by means of spores such as chlamydospores is desirable for wood, metal, glass, steel, plastic, concrete, finery, ceramic, or stone treatment.

These surfactants are surprisingly produced by the fungus for example when grown on a potato medium, preferably autoclaved. The potato medium is for example in combination with glucose and a vegetable- and/or animal oil or a derivative thereof, or a water-insoluble substance of C3 to C40, C4 to C32, C5 to C30, C6 to C28, C7 to C25, C8 to C23, C9 to C20 or C10 to C15 saturated or unsaturated fatty acid ester. The amount of the surfactant produced by the microorganism in the medium of added to the medium is for example from 2 g/l to 10 g/l, 3 g/l to 9 g/l or 5 g/l to 8 g/l. The process of production of surfactants goes along with a temporary disappearance of pigmentation at a certain stage of the fermentation.

The dissolved oxygen content ($DO_2$) remains within a range between 20% and 95%, 30% and 90%, 40% and 80% or 50% during the fermentation process in order to allow the growth of sufficient pigmented chlamydospores. For example the fungus produces up to 2 g/l to 10 g/l surfactant growing on a potato medium comprising a water-substance of C3 to C40, C4 to C32, C5 to C30, C6 to C28, C7 to C25, C8 to C23, C9 to C20 or C10 to C15 or the fungus produces up to 3 g/l to 9 g/l surfactant growing on a potato medium comprising a water-substance of C3 to C40, C4 to C32, C5 to C30, C6 to C28, C7 to C25, C8 to C23, C9 to C20 or C10 to C15 or the fungus produces up to 5 g/l to 8 g/l surfactant growing on a potato medium comprising a water-substance of C3 to C40, C4 to C32, C5 to C30, C6 to C28, C7 to C25, C8 to C23, C9 to C20 or C10 to C15. In each of these combinations the $DO_2$ remains in a range of 20% and 95%, 30% and 90%, 40% and 80% or 50%. Some even more preferred combinations of $DO_2$ conditions and fatty acids and the produced amounts of surfactants are shown in the following Table 1:

| Surfactants | Fatty acids 0.1% of fermentation liquid | Fatty acids 1% of fermentation liquid | Fatty acids 2% of fermentation liquid |
|---|---|---|---|
| 20%--90% $DO_2$ | 1 g/l | 1 g/l | 1 g/l |
| 30%-90% $DO_2$ | 2 g/l | 4 g/l | 5 g/l |
| 40%-90% $DO_2$ | 4 g/l | 7 g/l | 8 g/l |

A coating created by a method of the present invention remains stable on the surface at outdoor conditions, is not removable and not susceptible to microbial infection and degradation. The effect of the surfactants can for example be ascribed to the reduction of surface tension of the fungal suspension leading to improved wettability of the material surface and the creation of chemical interaction. This chemical interaction is dependent on adequate radiation which should comply at least for example UV radiation consisting of 50%-90% UV-A (380-315 nm) and 10%-50% UV-B (315-280 nm), or 60%-95% UV-A (380-315 nm) and 5%-40% UV-B (315-280 nm). If the radiation spectrum does not fulfil the requirements of the composition, adhesion and curing does not take place. The requirements of the composition depend on the compounds of the composition. For example a composition with a content of 2 g/l-10 g/l surfactants, 5 g/l-40 g/l biopolymers requires a radiation of 50%-90% UV-A (380-315 nm) and 10%-50% UV-B (315-280 nm)

The present invention refers to a viable coating based on a living microorganisms which can be controlled during all production steps and directly applied on a material such as the surface of the material. The applied microbial coating is creating one or more protecting layers, which are (for example biochemically) bound to each other and/or to the surface of the carrier material.

The coating composition consisting of or comprising a microbial suspension is produced for example in a biological micro-reactor (fermenter). The microbial suspension and the conditions of the fermenter are for example formulated according to the requirements e.g., of the material such as the material surface and its use. The fermentation is for example based on a single type of microorganism or the combination of two or more types of microorganisms.

A microorganism of the present invention is for example selected from the group consisting of fungus including yeast and bacterium or a combination thereof. The microorganism is for example a black yeast or a related fungus. The microorganism is for example selected from the group consisting of *Aureobasidium* (e.g., *Aureobasidium* spp., *Aureobasidium pullulans*), *Rhodotorula* (e.g., *Rhodotorula* spp.), *Lapidomyces*, *Superstratomyces*, *Sarcinomyces*, *Chrysosporium*, *Penicillium*, *Alternaria*, *Fusarium*, *Stachybotrys*, *Rhizospaera*, *Taphrina*, *Sydowia*, *Phacidiella*, *Pyrenochaeta*, *Phaeococcomyces*, *Knufia*, *Capronia*, *Cladosporium*, *Cryptococcus*, *Pleurophoma*, *Cynanodermella*, *Exophiala*, *Epicoccum* and *Didymellaceae* or a combination thereof. A preferred microorganism is for example *Aureobasidium* such as *Aureobasidium* spp, *Aureobasidium pullulans* and/or *Rhodotorula* such as e.g., *Rhodotorula* spp. The microorganism or at least specialized cells of the microorganism use for the present invention are for example characterized by UV-resistance, tolerance to climatic and/or weather changes (i.e., for example extreme temperature and/or moisture conditions). The microorganism does for example not degrade the material which forms the surface to which the microorganism is adhered to and/or growing on, but forms one or more protecting layers on the surface.

The microorganism is for example grown under an adequate standard fermentation condition. The term adequate standard fermentation condition refers to a fermentation which is carried out at e.g. a temperature between 25° C.-35° C., stirring speed between 50 and 700 rpm, air debit>1 l/min, $DO_2$ between 0% and 90%, pH controlled fluctuating between 2 and 7.

A microorganism use for the present invention is able to generate different types of cells such as a spore, e.g., a chlamydospore and a vegetative cell, wherein the vegetative cell is a growing cell. The microorganism is for example pigmented or comprises a mixture of pigmented and unpigmented cells. For example a spore such as a chlamydospore is pigmented and/or unpigmented, and a vegetative cell is pigmented or unpigmented, wherein the spore is for example equally or stronger pigmented than the vegetative cell or vice versa. The chlamydospore is for example of fungal or bacterial origin.

The term spore such as chlamydospore refers to a viable pigmented and/or unpigmented thick-walled spore with the potential to interact with additives, surfactants and physical factors for example radiation to produce useful polymers (e.g., EPS) during a fermentation process, a curing process and/or exposure to UV light.

Dormant cells are e.g. chlamydospores or other thick-walled pigmented cells which remain in a stable "resting" state which is achieved during fermentation. The viability remains under extreme conditions such as continuous surrounding of a liquid, hardly any oxygen availability over a longer period for example up to several years (e.g., 2-10 years), extreme pH (<3), lack of nutrients, lack of light or a combination thereof. Extreme temperature conditions for example temperature up to 90° C. or high radiation energy favours the formation of a spore such as a chlamydospore or other thick-walled pigmented cell.

These dormant cells are further characterised by a cell wall which is chemically inert and cannot be dissolved, disintegrated and/or penetrated under normal conditions by most of the known chemicals, e.g., solvents, alcohols or acids. The pigments from the cell walls of these chlamydospores or other thick-walled pigmented cells are therefore difficult or impossible to access.

The term "pre-activated" refers to a spore such as a chlamydospore or other thick-walled pigmented cell which is dormant, but able to react swiftly on triggers and produce desired extracellular polymeric substances under controlled conditions.

These substances are for example a surfactant from the group consisting of a lipopeptide, a lipid, a glycolipid, a uronic acid based polymer, heavy oil, e.g., mannitol oil (e.g., liamocin), siderophore, malic acids and/or a derivate thereof, polysorbates and/or a derivate thereof. Contrary to known processes this process can be carried out with "pre-activated" cells under extreme conditions on solid surfaces of different materials. In contrast to "normal" cells pre-activated cells have the potential to react in a desired, i.e., predictable way on a trigger which is deadly for "normal" cells like for example lack of water or strong UV-radiation. This property is created during the fermentation process but will be activated at a later stage which can be months or years.

The trigger to activate these cells are for example changes of the above mentioned conditions such as liquid, oxygen availability, pH, nutrients, light, radiation, temperature or a combination thereof. The "pre-activation" additionally or alternatively refers to the addition of chemicals to dormant spores such as chlamydospores or other thick-walled pigmented dormant cells. These chemicals are for example a compound of high and/or low molecular weight which is for example between 130 g/mol and 1500 g/mol (per repetitive unit), between 150 g/mol and 1350 g/mol (per repetitive unit), between 250 g/mol and 1200 g/mol (per repetitive unit), between 500 g/mol and 1100 g/mol (per repetitive unit), or between 750 g/mol and 1000 g/mol (per repetitive unit). The chemical is for example selected from the group consisting of a glycolipid (e.g., rhamnolipids, trehalolipids, sophorolipids), a lipopeptide, a lipoprotein, a phospholipid an essential oil, a polymalic acid (PMA), a liamocin or a combination thereof.

The pigment is for example secreted by the vegetative cells into the surrounding medium. The pigmentation system of the microorganism influences for example the surface appearance and results, e.g., in gloss, coloured or opaque appearance.

The pigment which is for example produced by the microorganism or is added to the microorganism is for example a biological pigment such as melanin or a derivative thereof e.g., eumelanin, pheomelanin, trichochromes, neuromelanin, polyketide, azaphilone such as monascin, ankaflavin, pentaketide, indol derivative, e.g., pityriacitrin, anthrachinone such as torosachrysine, naphtochinone such as viopurpurin, azaphilone such as monoascorubramine. The colour of the coating composition depends on the pigment of the cell and/or spore.

A microorganism of the present invention grows for example on a surface of a material under extreme climate conditions, but is not or only minimally affected by these conditions. Alternatively, the microorganism is even positively affected by extreme environments which results for example in increased cell growth wherein the cells have a thicker cell wall (i.e., resulting in larger cells) and/or pigment production.

All the steps of the method for the coating, the functional properties and/or appearance of the coating are controlled by selection of the adequate microorganism, of an additive such as a surfactant, a thickener, a carbon source or a combination thereof, and/or variation of the method steps.

An adequate microorganism for use in the present invention fulfils for example the following requirements:
- no degradation activity on the carrier material (e.g., not wood degradable and non-corrosive effects on e.g. metals)
- thermal tolerance for example in the range of >50° C. and <−20° C., and
- high moisture tolerance (i.e., viable at low and/or high water availability).

The microorganism suspension and/or the coating composition are producible in the range of small scale up to industrial scale. The microorganisms of the present invention are grown for example in a fermentation process in a bioreactor such as a standard fermenter. Such fermenters are known by a person skilled in the art.

The microorganism and the growth medium form for example a microorganism suspension such as a fungal suspension, a bacterial suspension or a combination thereof. The coating composition of the present invention consists of or comprises the microorganism suspension such as a fungal and/or bacterial suspension and optionally an additionally added compound of high and/or low molecular weight which is for example between 130 g/mol and 1500 g/mol (per repetitive unit), between 150 g/mol and 1350 g/mol (per repetitive unit), between 250 g/mol and 1200 g/mol (per repetitive unit), between 500 g/mol and 1100 g/mol (per repetitive unit), or between 750 g/mol and 1000 g/mol (per repetitive unit).

The growth medium consists of or comprises for example a carbohydrate such as a digestible carbohydrate, e.g., monosaccharide (e.g., glucose, fructose, xylose, galactose), disaccharide (e.g., sucrose, maltose, lactose, trehalose), oligosaccharide (e.g., maltodextrin, raffinose, stachyose), and/or polysaccharide (e.g., starch, cellulose, hemicellulose, pectin, glycogen). The growth medium alternatively or additionally consists of or comprises an organic substance for example from a herbal or animal source. A source for the organic substance is for example biological waste material, e.g., marc from straining fruit or vegetable such as remaining plant material from sugar production, wine production, juice production, e.g., fruit juice production, potato juice production etc. or a combination thereof.

During growth of the microorganism different types of cell may be produced such as pigmented and/or unpigmented vegetative cells as well as optionally pigmented and/or unpigmented spores such as chlamydospores. The different types of cells may have different properties influencing for example the adhesion of the coating composition and microorganism suspension, respectively, on the surface. The coating composition and microorganism suspension, respectively, is administered to a surface via any known method for the administration of a coating such as applying via a brush, roller, airbrush or any other industrial device in an industrial process for example impregnation systems for the application of stain on surfaces (e.g., wooden surfaces) including vacuum coating.

The growth of the microorganism, i.e., the fermentation process is for example controlled to reach a desired texture of the coating composition and microorganism suspension, respectively, based on the number and/or ratio of pigmented and unpigmented vegetative cells and spores (FIG. 1) for example from a fungus such as *Aureobasidium*, e.g., *Aureobasidium pullulans* or spp. The pigment is either in the cell, in the cell membrane or freely floating in the growth medium (e.g., secreted in the medium), i.e., optionally in the suspension of the microorganism and the coating composition, respectively. For example, in order to achieve reasonable pigmentation and an active stable suspension of a microorganism such as a fungus, a mix of vegetative pigmented- and non-pigmented cells and spores such as chlamydospores is used. A coating composition of the present invention consists of or comprises for example such suspension. Examples for such mixtures of cells are shown in the following Table 2:

TABLE 2

Cell ratios in a fungal suspension of *Aureobasidium pullulans* after fermentation (none of the mixtures exceeds 100% in the total composition).

| | Vegetative cells (unpigmented) | Vegetative cells (pigmented) | Chlamydospores (pigmented) |
|---|---|---|---|
| Suspension 1 | 10-20% | 50-70% | 10-40% |
| Suspension 2 | 10-40% | 50-70% | 10-20% |
| Suspension 3 | 10-35% | 10-35% | 50-70% |
| Suspension 4 | 50-70% | 10-35% | 10-35% |

The quality of the coating composition is for example influenced by the cell types of the microorganism such as the combination of pigmented and/or unpigmented vegetative cells and pigmented and/or unpigmented pre-activated dormant thick-walled cells such as chlamydospores.

Further, a surfactant such as a biosurfactant of high and/or low molecular weight which is for example between 130 g/mol (per repetitive unit, low) and 1800 g/mol (per repetitive unit, high) influences the adhesion and/or growth of the microorganism on the surface. Low molecular weight molecules might lower surface and interfacial tensions whereas high molecular weight polymers potentially improve adhesion to surfaces. The surfactant such as a biosurfactant is for example produced by the microorganism itself. It is either kept in or on the cell and/or is secreted into the medium such as the growth medium. The surfactant or reaction products thereof can for example be produced or secreted by the microorganisms during the fermentation process, during an application process, during a curing process or during the exposure of the coating layers on the surface of a carrier material.

Alternatively or in addition, a surfactant is added to the growth medium and/or the coating composition. Examples of surfactants of high or low molecular weight are lipopeptide (e.g. Liamocin oil, Aureosurfactin or 3-deoxyaureosurfactin), glycolipid, lipid, uronic acid based polymer, heavy oil such as mannitol oil (e.g., liamocin), siderophore, malic acid and/or derivates thereof, polysorbate and/or derivates thereof or a combination thereof.

Another factor influencing the adhesion and/or growth of the microorganism is the presence of an extracellular polymeric substance (EPS). Examples of EPS are water-soluble binders like polysaccharide polymers such as hetero polysaccharides, chitin, pullulan, proteoglycan such as β-glucan, polymalic acid, glycoprotein, chitin or a combination thereof. The EPS is produced by the microorganism and/or added to the growth medium and/or coating composition. The EPS belongs for example to the group of binders.

The production of a surfactant such as a biosurfactant and/or of a binder such as an EPS by the microorganism is for example influenced, i.e., initiated or increased by compounds of the growth medium. Such compounds are for example a biological waste material, e.g., marc from straining fruit or vegetable such as remaining plant material from sugar production, wine production, juice production such as fruit juice production, potato juice production etc., or a combination thereof.

The adhesion to and/or growth of the microorganism on the surface is for example further improved by increased viscosity of the coating composition and the suspension of the microorganism, respectively. An increase of the viscosity is for example reached by addition of a biological compatible substance such as a thickener, e.g., selected from the group consisting of alginic acid and/or a derivate thereof, agar-agar, carrageenan or a derivate thereof, locust bean gum (LBG), tara gum, tragacanthin, gum arabic, gum karaya, xanthan, or tannins from e.g. T. spinose, gellan gum or a combination thereof.

The compound to increase the viscosity is for example in an amount of 0.5 to 15%, 1 to 14%, 3 to 13%, 5 to 14%, 10 to 15% or up to a maximum of 1%, 50%, 100%, 15%, 200% or 25% of the total mass of the coating composition. The viscosity is for example in a range of 100 to 5.000 mPa, 500 to 4.500 mPa, 1.000 to 4.000 mPa, 1.500 to 3.500 mPa or 2.000 to 3.000 mPa at 20° C.

The suspension of the microorganism such as a fungal and/or bacterial suspension for example consists of or comprises the microorganism and its growth medium. Thus, the microorganism is not separated from the growth medium, no washing and/or drying step is required to reach the suspension of the microorganism forming the coating composition of the present invention. This reduces the use of water and enables cost reduction due to the absence of a separation step.

Alternatively, if the microorganism should be isolated for example in case of a long distance transport to reduce transport costs, the microorganism is for example separated from the growth medium, e.g., via freeze-drying techniques. The isolated microorganism is then dissolved for example in oil comprising binders such as pullulan, chitin, proteoglycan, β-glucan, polymalic acid, glycoprotein or a combination thereof forming a suspension. Optionally, a water soluble and/or a water-insoluble binder is added to the suspension. Such compound is for example pullulan or another compound originally produced by the microorganism and/or added to the suspension. Optionally, the microorganism is dissolved in the coating composition.

Moreover, the suspension of the microorganism and/or the coating composition optionally comprises an additive such as a thickener, e.g., alginic acid and/or a derivate thereof, agar-agar, carrageenan and/or a derivate thereof, locust bean gum (LBG), tara gum, tragacanthin, gum arabic, gum karaya, xanthan, tannins from e.g. T. spinose, gellan gum, or a combination thereof, an emulsifier and/or a surfactant, e.g., polysorbate, a sorbitane, a pectine, a glucomannan or a combination thereof. The additive is for example produced during fermentation of the microorganism, it is added to the suspension of the microorganism after fermentation and/or it is produced in situ during the maturing and/or curing process of the microbial coating layer, e.g., on the surface.

After a certain while the microbial coating may need to be refreshed using a nutrition medium consisting of or comprising pigmented and/or unpigmented spores such as chlamydospores and optionally pigmented and/or unpigmented vegetative cells; or pigmented and/or unpigmented vegetative cells and optionally pigmented and/or unpigmented spores such as chlamydospores. Optionally the nutrition medium comprises for example acyclic branched or unbranched hydrocarbons such as an alkane.

Alternatively or in addition, the nutrition medium consists of or comprises for example a water-insoluble substance, i.e., a substance which prevents or at least slows down the penetration of liquid water into the surface. The water-insoluble substance consists of or comprises for example an organic compound, e.g., selected from the group consisting of a mineral oil, wax, vegetable- and/or animal oil, including combinations and/or derivatives thereof. Further examples of the water-insoluble substance are C4 to C32 saturated or unsaturated fatty acid ester for example of a fatty acid comprising a polyol, such as glycerol. Additional examples of the water-insoluble substance are oils extracted from a seed or fruit such as vegetable oils (for example film forming), e.g., linseed oil, hempseed oil, olive oil or a combination thereof.

Optionally, the water-insoluble substance comprises one or more other additives for example selected from the group consisting of amino acids or monosaccharides such as fructose, disaccharides e.g. maltose oligo- or polysaccharides such as amylose, amylopectin or, pentosanes such as pentose, arabinose or xylose And pentosane such as pentose, arabinose or xylose or a combination thereof, which optionally form a nutrient for the microorganism.

Table 3 shows examples of coating compositions of the present invention comprising a microorganism such as *Aureobasidium* (none of the mixtures will exceed 100% in the total composition):

| Typical composition | Waterbased fungal suspension | Thickener | Nutrients | Emulgator |
|---|---|---|---|---|
| Variant 1 | 30-40% | 1-5% | 40-60% | <10% |
| Variant 2 | 60-70% | 1-8% | 10-20% | <7% |
| Variant 3 | 70-80% | 1-10% | 5-20% | <5% |

The microorganism suspension and the coating composition, respectively, of the present invention shows improved drying and adhesion properties on surfaces. Appropriate surfaces are for example wood, metal, steel, plastic, concrete, finery, ceramic, stone or any other material. The drying and/or adhesion properties of the coating composition forming the microbial coating are for example improved by a maturing process at natural and/or artificial radiation, applying high temperatures or a combination thereof. These temperatures are for example in the range of 20° C. to 250° C., 30° C. to 240° C., 40° C. to 220° C., 50° C. to 180° C., 60° C. to 160° C., 65° C. to 150° C., 70° C. to 140° C., 80° C. to 130° C., 90° C. to 120° C., 95° C. to 100° C. or 110° C., or 20° C., 30° C., 40° C., 50° C., 60° C., 70° C., 80° C., 90° C., 100° C., 110° C., 120° C., 140° C., 150° C., 160° C., 200° C. or 250° C.

Radiation is for example UV radiation consisting for example of 50%-90% UV-A (e.g., 380-315 nm) and 10%-50% UV-B (e.g., 315-280 nm), or 60%-95% UV-A (e.g., 380-315 nm) and 5%-40% UV-B (e.g., 315-280 nm). Optionally UV-radiation with a wave length in a range of 200 to 400 nm is used additionally. Alternative radiations are natural radiation of the environment (FIG. 2), radiation for example produced by LED lamps having different spectra, UV-radiation, e.g., based on mercury or iron UV lamps, or a combination thereof.

Typically, energy between 0 to 5000 $mW/cm^2$, e.g., 0 to 500 $mW/cm^2$ or 500 to 5000 $mW/cm^2$ is applied to the coating composition via radiation. The energy is for example applied over a time period of 5 sec to 300 sec, of 5 min. to 24 h, 10 min. to 20 h, 15 min. to 15 h, 30 min. to 10 h, or 1 h to 5 h. Sometimes it is advantageous to repeat energy application in one or more additional cycles for example in the same or a different time period. Optionally a recovery period takes place between the cycles allowing for example the fungus and/or bacteria to recover.

Maturing and/or curing of the coating composition on the surface is for example based on a combination of in situ production of binding polymers, polymerisation, drying or a combination thereof through added energy for example UV-radiation, optionally in addition to water evaporation. Optionally, the microorganism is for example growing into the cells of the surface, e.g., of a wooden surface without destroying, i.e., degrading the surface.

The coating composition comprises for example soot and/or graphite to stabilize e.g., dark, black color. Expandable graphite for example results in a substantially improved flame retardation of the biological coating. Due to the similarity of the color of the soot or graphite and the (relatively dark) melanin in the cells of the microorganism no esthetical interference appears, but also no biological interference with the cells of the microorganism is detectable.

The microbial coating of the present invention creates one or more protecting layers which have for example a total thickness in the range of about 1 to 1000 μm, 10 to 900 μm, 20 to 800 μm, 30 to 700 μm, 40 to 600 μm, 50 to 500 μm, 60 to 400 μm, 70 to 300 μm, 80 to 200 μm, 90 to 150 μm or at least 0.1 to 100 μm, at least 0.3 μm to 90 μm, at least 0.5 μm to 80 μm, at least 0.8 μm to 70 μm, at least 1 μm to 60 μm or at least 5 to 50 μm. Such a layer thickness has been found to contribute to a desired evenness of the microbial coating.

Material comprising a microbial coating of the present invention is for example used as a construction or building material. It is for example used in outdoor applications for example in applications without soil contact such as garden furniture, fence, facade elements or cladding, which is for example very useful in the case of wooden facades of skyscrapers made e.g., of CLT (cross laminated timber). Alternatively, it is for example used in outdoor applications for example in applications with soil contact such as sleepers, poles e.g., fence poles, vineyard poles or foundation piles. After treatment with a coating composition according to the present invention the service life is significantly increased.

The coating of the present invention is also an anti-corrosion coating as shown for example in FIG. 8. Material such as metal comprising one or more microbial coating layers are protected of corrosion, e.g., corrosion is at least reduced. Metals comprising a coating of the present invention are for example metals in different compositions or alloys, for example ferrous and non-ferrous metals like steel aluminum alloys, or magnesium alloys of mixtures thereof. The treatment of these surfaces is useful in corrosion inhibition, reduction of maintenance of civil infrastructure, building industry, car-, railway-, machine- and ship-industry. Potential corrosion inhibition might be further useful in offshore, storage tanks or pipelines.

The coating composition of the present invention is for example administered to fresh or aged surfaces such as fresh or aged wood or metal surfaces. Moreover, on a surface such as a wood or metal surface which for example has been already treated with a conventional coating the coating composition of the present invention can be directly applied. This is very useful in case of e.g. renovation of existing surfaces such as garden fences or facades.

Material comprising a microbial coating of the present invention has a durable homogenous surface colour and a long-term resistance for example against degrading microorganisms such as a microorganism causing rot including brown rot, withe rot and soft rot of wood. Additionally, material coated with the coating composition of the present invention is resistant against surface degrading animals, e.g., wooden surface degrading animals such as snails, wasps or other insects.

As the coating composition results in reduced water uptake of the coated material, it has significantly less shrinks or swells and/or significantly less cracks and checks. Furthermore, hardly any or even no UV degradation of the material coated with the coating composition of the present invention is detectable.

Advantageously, the coating composition will never have to be removed for example due to aging. For maintenance and refreshing, respectively, only the nutrition medium optionally enriched with chlamydospores has to be applied.

Advantageously, the coating composition can be used to be applied in one or more coating layers on metal surfaces to inhibit and or/reduce corrosion in a remedial treatment (e.g., FIG. 8).

Furthermore, the coating composition is used to preserve (preventive) metal compositions/alloy surfaces from a degradation process caused by another microorganism, water and oxidation and/or UV-radiation.

The microorganism is for example grown in potato medium to produce a surfactant.

Potato medium such as standard potato dextrose medium is well known by a skilled person.

A potato medium comprises or consists of for example:

900 ml Potato Dextrose Broth as starting medium
addition of 24 g/l Potato Dextrose Broth,
48 g/l Glucose,
9.3 g/l Ammonium Sulphate ($(NH_4)_2SO_4$,
0.9 g/l Potassium dihydrogen phosphate ($KH_2PO_4$)
10 g/l carbon source e.g. oil and/or surfactant and/or binder Table 4 shows an exemplary pump adjustment in time (h) for a typical fermentation process for example in potato medium:

| Pump adjustment | Time (h) |
|---|---|
| 0% | 0.0 |
| 35% | 41.5 |
| 45% | 164.5 |
| 60% | 171.0 |
| 70% | 175.5 |
| 100% | 191.8 |
| 0% | 199.0 |

For example fermentation takes place in a fed batch fermenter such as a 4 liter fed batch fermenter.

EXAMPLE

The following example illustrate an embodiment of the present invention, but the invention is not limited to this example.

Example 1

A coating composition according to the present invention was applied to a wooden surface, wherein the composition lacks surfactants (see FIG. 9A) or comprises surfactants (see FIG. 9C). The mass of coatings applied was between 5.1 and 5.9 gram. The coated wood was treated at 50° C. with UV radiation having an intensity of 0.68 W/$m^2$ and a wavelength of 340 nm (UV A) in an UV chamber, i.e., in a QUV cabinet (Q-lab) to imitate aging of the wood. The power of the UV lamp was 40 W.

The wash-off procedure via water spraying was adjusted to 5 minutes (once) and applied after 6 days exposure to UV-radiation (for good samples) and 24 hours (for poor samples) of the coated wood.

Filter paper was brought to the wooden surface. If the composition lacks a surfactant, the coating is removed already by the water spraying (see FIG. 9A) and further by the contact with the filter paper. Black coating is detectable on the filter paper (see FIG. 9B). The composition comprising a surfactant is not removable by the water spraying (see FIG. 9C) and the filter paper which was brought in contact with the coating on the wooden surface shows hardly any coating.

The invention claimed is:

1. A coating composition comprising a suspension of a fungus, wherein the suspension comprises 10-35% pigmented vegetative cells, 10-35% unpigmented vegetative cells, 50-70% pre-activated dormant chlamydospores of the fungus, and a biosurfactant produced by the fungus, wherein the biosurfactant is in an amount of 2 g/L to 10 g/L and has a molecular weight ranging from 130 g/mol to 1500 g/mol per repetitive unit, wherein the production of the biosurfactant is initiated by fatty acids and a dissolved oxygen content ($DO_2$) in a range from 30% to 90%, wherein the fungus is *Aureobasidium*.

2. The coating composition of claim 1, wherein the *Aureobasidium* is *Aureobasidium pullulans*.

3. The coating composition of claim 2, wherein the biosurfactant is aureosurfactin.

4. The coating composition according to claim 1, further comprising a water-soluble binder, a water-insoluble binder, a thickener or a combination thereof.

5. The coating composition according to claim 1, further comprising a binder, wherein the binder is an extracellular polymeric substance (EPS).

6. The coating composition according to claim 1, further comprising a thickener, wherein the thickener is selected from an aliginic acid, agar-agar, a carrageenan, locust bean gum (LBG), tara gum, tragacanthin, gum arabic, gum karaya, xanthan, tannins, gellan gum, and combinations thereof.

7. The coating composition according to claim 1, wherein the viscosity of the coating composition is in the range of 100 to 3.000 mPa at 20° C.

8. A method of coating a material, comprising the steps of:
applying to the coating composition according to claim 1 to the surface of the material at a temperature above 20° C.; and
drying the coating composition via natural or artificial radiation applying energy in the range of 50 to 5.000 $mW/cm^2$.

9. The method of claim 8, wherein UV radiation is applied consisting of 50%-90% UV-A and 10-50% UV-B, or 60%-95% UV-A and 5%-40% UV-B.

10. The method according to claim 8, wherein the material is selected from the group consisting of wood, metal, steel, plastic, concrete, finery, ceramic, stone and combinations thereof.

11. The method according to claim 8, wherein the coating composition is applied to the material forming one or more coating layers having a thickness in the range of 0.1 to 1000 μm.

12. A coated material obtainable by the method according to claim 8.

13. A method of refreshing the coating of the coated material according to claim 12, wherein a nutrition medium is applied to the coated material, the nutrition medium comprising mineral oil, wax, a vegetable oil and/or an animal oil a water-soluble substance of C4 to C32 saturated or unsaturated fatty acid ester, an amino acid, a pentosane or a combination thereof, and optionally a pigmented vegetative cell, an unpigmented vegetative cell and a pigmented dormant chlamydospore of a microorganism.

14. The coating composition according to claim 5, wherein the EPS is selected from the group consisting of a hetero polysaccharide, chitin, pullulan, proteoglycan, β-glucan, polymalic acid, a uronic acid based polymer, glycoprotein, and combinations thereof.

* * * * *